(12) United States Patent
Blevins et al.

(10) Patent No.: US 6,420,505 B1
(45) Date of Patent: Jul. 16, 2002

(54) PROCESS FOR PREPARING THIOSULFATE SALT POLYMERS

(75) Inventors: Richard W. Blevins; Shiying Zheng, both of Rochester, NY (US)

(73) Assignee: Eastman Kodak Company, Rochester, NY (US)

( * ) Notice: Subject to any disclaimer, the term of this patent is extended or adjusted under 35 U.S.C. 154(b) by 0 days.

(21) Appl. No.: 09/885,595

(22) Filed: Jun. 20, 2001

(51) Int. Cl.$^7$ ................................................ C08F 28/02
(52) U.S. Cl. ........................................ 526/287; 526/75
(58) Field of Search .................... 525/333.3, 333.5, 525/344; 526/287, 75

(56) References Cited

U.S. PATENT DOCUMENTS

| | | |
|---|---|---|
| 3,706,706 A | 12/1972 | Vandenberg |
| 4,587,296 A | 5/1986 | Moniotte |
| 4,895,917 A | 1/1990 | Gruning ............... 528/10 |
| 5,985,514 A | 11/1999 | Zheng et al. ............ 430/270.1 |
| 6,136,503 A | 10/2000 | Zheng et al. ............ 430/270.1 |

FOREIGN PATENT DOCUMENTS

| | | | |
|---|---|---|---|
| DE | 1143330 | * | 2/1963 |

OTHER PUBLICATIONS

Ronald W. Feldstein, "Bunte Salt Polymers, Synthesis, Reactivity and Properties", American University, 1971.

Shelby F. Thames, J. Coat. Technol., "Bunt Salts as Crosslinking Agents in Thermosetting Water–Borne Polymers", 1983, vol. 55, pp. 33–39.

Thames et al, Water–Borne and Higher–Solids Coatings Symposium, "Thiosulfate Containing Polymers as Water–Borne Themosetting Coatings II", 1985, 12, pp. 5–7.

* cited by examiner

*Primary Examiner*—Christopher Henderson
(74) *Attorney, Agent, or Firm*—Sarah Meeks Roberts

(57) ABSTRACT

This invention relates to a method of preparing a thiosulfate salt containing polymer comprising reacting at least one thiosulfate salt with at least one halogenated styrenic monomer to form a styrenic thiosulfate salt monomer represented by Formula (1);

Formula (1)

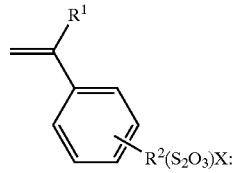

wherein X is a cationic counter ion; $R^1$ is a substituent; and $R^2$ is a divalent linking group; and polymerizing the styrenic thiosulfate salt monomer in the presence of an initiator.

4 Claims, No Drawings

PROCESS FOR PREPARING THIOSULFATE SALT POLYMERS

FIELD OF THE INVENTION

This invention relates to an improved polymerization process for preparing pendant thiosulfate (Bunte salt) containing polymers derived from styrenic thiosulfate monomers. The thiosulfate salt monomers may be homopolymerized or copolymerized with one or more ethylenically unsaturated comonomers. In particular, this invention relates to an efficient process wherein a thiosulfate salt monomer is made but not isolated or further purified prior to homopolymerization alone or copolymerization with other monomers.

BACKGROUND OF THE INVENTION

Water soluble polymers formed from thiosulfate salts are useful in a variety of current and potential applications including their use to cross-link or otherwise modify the properties of natural polymer fibers such as wool, cellulosics and leather, and as water-insoluble polymeric sulfur dyes. They are also used in the coating industry and for the manufacture of lithographic printing plates.

H. Bunte first prepared organic thiosulfates or Bunte salts in 1874 with a process which utilized aqueous solutions at an elevated temperature.

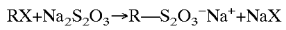

$RX + Na_2S_2O_3 \rightarrow R\text{---}S_2O_3^- Na^+ + NaX$

This method can also be applied to secondary alkyl halides but not to tertiary halides. Other known methods for the preparation of thiosulfate salts are discussed in U.S. Pat. No. 4,587,296 (P. Moniotte).

Earlier studies have demonstrated that thiosulfate salts can be incorporated into polymers such as poly (epichlorohydrin) by reaction of a chloride group with thiosulfate. Feldstein, in R. W. Feldstein, "Bunte Salt Polymers. Synthesis, Reactivity and Properties", The American University, 1971, described two synthetic routes to thiosulfate polymers. One method involved the ring opening of glycidyl methacrylate reacted with sodium thiosulfonate, thereby forming a thiosulfate monomer which was then polymerized. The second approach described by Feldstein started with a preformed polystyrene which was chloromethylated and then converted to the thiosulfate salt using magnesium thiosulfate in dimethylformamide (DMF). Feldstein's attempts to isolate a styrenic thiosulfate salt monomer or polymer were unsuccessful.

More systematic work in the area of water-soluble or water-dispersible thiosulfate salt polymers for coatings was described by Thames and coworkers (J. Coat. Technol. 1983, 55, 33–39; Proc. Water-Borne Higher-Solids Coat. Symp. 1985, 12, 5–7). Thames described the synthesis of thiosulfate polymers by using aminoethane thiosulfuric acid in the nucleophilic displacement of alkyl halides, such as epichlorohydrin in DMF/water; or by reacting thiosulfates with either the epoxide ring of glycidyl-containing monomers or with acid chlorides. The polymers obtained by these processes were of low molecular weight. Additionally, their synthesis involved the use of undesirable solvents such as tetrahydrofuran (THF) or dimethylformamide (DMF) and required multiple purification steps.

The most common commercial applications for thiosulfate polymers involve thiosulfate terminated polyethers. In particular, the patents of both Gruning U.S. Pat. No. 4,895,917 and Vandenberg U.S. Pat. No. 3,706,706 describe the modification and use of preexisting polymers with sodium thiosulfate to form thiosulfate polymers. U.S. Pat. Nos. 5,985,514 and 6,136,503 describe two general approaches to manufacturing thiosulfate salt polymers. In the first approach, a thiosulfate salt monomer is made in a water/alcohol mixture, isolated, purified, and then redissolved with a second monomer to make a copolymer. This approach has the disadvantage of high waste generation, low yield, and a long and somewhat difficult reaction sequence. In the second approach to thiosulfate salt polymers, a preformed homopolymer or copolymer containing a halogenated substituent is either purchased or made in an organic solvent. It is then precipitated and isolated, and then redissolved in DMF/water in order to react with sodium thiosulfate and form a thiosulfate salt polymer. Again, this approach has several disadvantages including the use of undesirable organic solvents, such as toluene, THF, dimethyl sulfoxide (DMSO) and DMF, high waste generation, and a limited number of available starting commercial polymers.

In general, the undesirable proclivity of thiosulfate salts to react with activated double bonds such as acrylic and methacrylic acid derivative monomers has limited their usefulness with this class of monomers. Further, the use of an unpurified monomer generally prevents the conversion of the monomer by free radical polymerization to a thiosulfate salt polymer or limits the size of the polymer to low molecular weight oligimers.

It is, therefore, highly desirable to provide simpler and more robust methods for the preparation of thiosulfate salt monomers and their subsequent incorporation into polymers. It is particularly desirable that such methods be environmentally friendly and cost effective.

SUMMARY OF THE INVENTION

This invention provides a method of preparing a thiosulfate salt containing polymer comprising reacting at least one thiosulfate salt with at least one halogenated styrenic monomer to form a styrenic thiosulfate salt monomer represented by Formula (1);

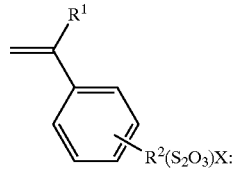

Formula (1)

wherein X is a cationic counter ion; $R^1$ is a substituent; and $R^2$ is a divalent linking group; and polymerizing the styrenic thiosulfate salt monomer in the presence of an initiator.

The present invention provides a simple and robust process for the production of vinyl aromatic hydrocarbon (also known as styrenic) thiosulfate salt monomers which can then be utilized in a polymerization process without purifying the intermediate thiosulfate salt monomer(s). This process utilizes environmentally friendly solvents, it reduces manufacturing costs, and it improves the throughput and yield of the monomers and the final polymerized materials. Thiosulfate salt polymers are considerably easier to prepare and purify with the current invention than with processes described in the prior art. Because the inventive process is commercially viable, it will increase the availability and variety of homopolymers and copolymers containing thiosulfates.

DETAILED DESCRIPTION OF THE INVENTION

The initial step of the process of the invention comprises reacting at least one thiosulfate salt with at least one halogenated styrenic monomer to form a styrenic thiosulfate salt monomer represented by Formula (1).

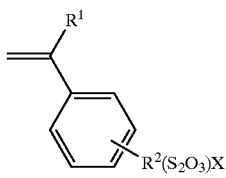

Formula (1)

X is a proton or a cationic counter ion. Preferably X is a metal ion, particularly an alkali metal ion, or an ammonium ion. Examples of suitable cationic counter ions include sodium, potassium, magnesium, ammonium, barium, lithium, calcium, cesium, zinc, diazonium, iodonium, pyridinium, phosphonium, sulfonium, or 2-benzyl-2-imidazoline. Preferred cationic counter ions are sodium, potassium, and ammonium.

$R^1$ is any suitable substituent which does not interfere with either the process of preparing the monomers or the final polymerization process. In one suitable embodiment $R^1$ is either a hydrogen or halide atom; a substituted or unsubstituted alkyl group having 1 to 16 carbon atoms, more preferably having 1 to 8 carbon atoms; a substituted or unsubstituted aryl group having 6 to 16 carbons (such as a phenyl or naphthyl group), more preferably having 6 to 10 carbon atoms; a substituted or unsubstituted heteraryl group of 4 to 16 atoms; or a cyano group. Preferably $R^1$ is either a hydrogen or an alkyl group having 1 to 4 carbon atoms, such as a methyl, ethyl, or butyl group.

$R^2$ is a divalent linking group. Preferably $R^2$ is a substituted or unsubstituted linear, branched or cyclic alkylene group having 1 to 8 carbon atoms that can have one or more oxygen, nitrogen, or sulfur atoms in the chain, or a substituted or unsubstituted arylenealkylene group having 7 to 16 carbons. More preferably $R^2$ is a substituted or unsubstituted linear, branched or cyclic alkylene group having 1 to 8 carbon atoms and most preferably having 1 to 4 carbon atoms, such as methylene, ethylene, isopropylene, etc.

When reference in this application is made to a particular group, unless otherwise specifically stated, the group may itself be unsubstituted or substituted with one or more substituents (up to the maximum possible number). For example, "alkyl" group refers to a substituted or unsubstituted alkyl group, while "benzene" refers to a substituted or unsubstituted benzene (with up to six substituents). The substituent may be itself substituted or unsubstituted.

Generally, unless otherwise specifically stated, substituents include any substituents, whether substituted or unsubstituted, which do not destroy properties necessary for the described utility. Examples of substituents include known substituents such as: halogen, for example, chloro, fluoro, bromo, iodo, alkoxy, particularly those "lower alkyl" (that is, with 1 to 6 carbon atoms, for example, methoxy, ethoxy; substituted or unsubstituted alkyl, particularly lower alkyl (for example, methyl, trifluoromethyl); thioalkyl (for example, methylthio or ethylthio), particularly either of those with 1 to 6 carbon atoms; substituted and unsubstituted aryl, particularly those having from 6 to 20 carbon atoms (for example, phenyl); and substituted or unsubstituted heteroaryl, particularly those having a 5- or 6-membered ring containing 1 to 3 heteroatoms selected from N, O, or S (for example, pyridyl, thienyl, furyl, pyrrolyl); acid or acid salt groups such as any of those described below; and others known in the art. Alkyl substituents may specifically include "lower alkyl" (that is, having 1–6 carbon atoms), for example, methyl, ethyl, and the like. Further, with regard to any alkyl group or alkylene group, it will be understood that these can be branched or unbranched and include ring structures.

Any suitable thiosulfate salt, or its hydrate, which can produce the monomer as described above, may be used in this process. Examples of suitable thiosulfate salts include sodium thiosulfate, potassium thiosulfate, magnesium thiosulfate, ammonium thiosulfate, barium thiosulfate, 2-benzyl-2-imidazoline thiosulfate, or their hydrates. More than one thiosulfate salt may be used at the same time.

The thiosulfate salt is reacted with an equivalent amount of at least one halogenated styrenic monomer such as 3-vinyl benzyl chloride, 4-vinyl benzyl chloride, 4-vinyl benzyl bromide, 1-(2-chloroethyl)-4-vinyl benzene, or 1-(3-bromopropyl)-4-vinyl benzene. By "equivalent" it is meant the moles of thiosulfate salt that will react with one mole of the halogenated styrenic monomer. Generally the thiosulfate monomer is prepared in a mixture of water and at least one water miscible solvent. Examples of suitable solvents include acetone, 2-butanone, methanol, ethanol, n-propanol, isopropanol, n-butanol, 2-butanol, tert-butanol, methyl sulfoxide, dimethyl formamide, n-methyl pyrrolidinone, ethylene glycol, methyl ethyl ketone, tetrahydrofuran, di(propylene glycol)methyl ether, and propylene glycol. Typically, the thiosulfate salt is dissolved in water and combined with a halogenated styrenic monomer dissolved in the water miscible solvent. More preferred solvents include acetone or an alcohol such as methanol, ethanol, n-propanol, or isopropanol. The thiosulfate salt/halogenated styrenic monomer solution is reacted at a temperature of from 10° C.–100° C., and more preferably from 50° C.–80° C., with stirring, for a period of time sufficient to convert the styrenic monomer to a thiosulfate salt monomer, typically from 1 to 24 hours, with heating. In a preferred embodiment of the process of the present invention, the styrenic thiosulfate salt monomer is used to form a thioulfate salt containing polymer without further purification or isolation.

The thiosulfate monomer may be further diluted with additional solvent and is then homopolymerized or copolymerized with one or more ethylenically unsaturated monomers in the presence of an initiator. The initiator and optional other monomers may be added at once in a batch process or fed concurrently over time in a semicontinuous process. For example, either the initiator, the optional other monomers, or both may be introduced separately into the reaction mixture over suitable period of time up to the entire length of the reaction period. The temperature of the reaction mixture during the polymerization should be maintained from about −10° C. to about 130° C., more preferably from about 10° C. to about 100° C., and most preferably from 50° C. to about 80° C. The reaction mixture pressure should be maintained at from about atmospheric to about 40 pounds per square inch gauge (psig). Preferably, the reaction mixture pressure is maintained at or slightly above atmospheric pressure. The polymerization may be conducted in air or any inert atmosphere such as nitrogen or argon. The reaction is allowed to continue for a time sufficient to allow the homopolymer or copolymer product to form. The process time can be seconds, or up to 72 or more hours, depending on the initiator, reaction conditions, and whether the process is batch or semicontinuous. In one embodiment the polymerization process takes place in the presence of a surfactant.

Suitable initiators for the process of the present invention are any conventional free radical generating initiators, redox initiators, and combinations thereof. The total initiator added to the reaction mixture should be from about 0.001 to about 5 weight percent based on the total amount of monomer added. Preferred free radical initiators are peroxides or azos. Specific examples of free-radical initiators include, for example, hydrogen peroxide, t-butyl hydroperoxide, ditertiary butyl peroxide, ammonium persulfate, potassium persulfate, sodium persulfate, sodium perphosphate, ammonium perphosphate, tertiary-amyl hydroperoxide, 1,1'-azobis(cyclohexanecarbonitrile), methylethyl ketone peroxide, 2,2-azobis(cyanovaleric acid), benzoyl peroxide, cumene hydroperoxide; azobisisobutyronitrile (AIBN), 2,2'-azobis(2,4-dimethylpentanenitrile), lauroyl peroxide, 2,2'-azobis(2-methylbutanenitrile), 2,5-dimethyl-2,5-di(t-butylperoxy)hexane, the dialkyl peroxides, e.g., diethyl peroxide, dipropyl peroxide, dilauryl peroxide, dioleyl peroxide, distearyl peroxide, di-(tertiary-butyl) peroxide and di-(tertiary-amyl) peroxide, such peroxides often being designated as ethyl, propyl, lauryl, oleyl, stearyl, tertiary-butyl and tertiary-amyl peroxides; the alkyl hydrogen peroxides, e.g., tertiary-butyl hydrogen peroxide (tertiary-butyl hydroperoxide), tertiary-amyl hydrogen peroxide (tertiary-amyl hydroperoxide), etc.; symmetrical diacyl peroxides, for instance, peroxides which commonly are known under such names as acetyl peroxide, propionyl peroxide, lauroyl peroxide, stearoyl peroxide, malonyl peroxide, succinyl peroxide, phthaloyl peroxide, benzoyl peroxide, etc.; fatty oil acid peroxides, e.g., coconut oil acid peroxides, etc, and the like. More preferred free radical initiator include 2,2'-azobis(2,4-dimethylpentanenitrile), and 2,2'-azobis(2-methylpropanenitrile).

There is no particular limitation concerning the variety of additional monomers that can be incorporated along with the thiosulfate salt monomer of the present invention. Any single comonomer or combination of comonomers chosen from the known polymerizable ethylenically unsaturated monomers containing the polymerizable C=C group can be used. The acrylate class of monomers specifically includes, for example, methyl methacrylate, acrylic acid, methacrylic acid, methyl ethylacrylate, methyl acrylate, ethyl acrylate, propyl acrylate, n-butyl acrylate, glycidyl acrylate, t-butyl acrylate, n-amyl acrylate, n-hexyl acrylate, 2-ethylhexyl acrylate, octadecyl acrylate, o-tolyl acrylate, benzyl acrylate, cyclohexyl acrylate, 2-chloroethyl acrylate, vinyl acrylate, allyl acrylate, isobutenyl acrylate, 1-butenyl acrylate, hydroxyethyl acrylate, hydroxypropyl acrylate, hydroxyethyl methacrylate, and hydroxypropyl methacrylate crotyl acrylate, 2-butenyl acrylate, cinnamyl acrylate, 3-cyclopentenyl acrylate, citronellyl acrylate, geranyl acrylate, 5-norbornen-2-yl-methyl acrylate, β-chloroallyl acrylate or any of the methacrylates of the previously identified acrylate compounds and the like. Other optional monomers which are useful in the process of the present invention include acrylamide, methacrylamide, N-tertiary-butylacrylamide, N-methylacrylamide, N,N-dimethylacrylamide; acrylonitrile, methacrylonitrile, vinylidene chloride, vinyl butyral, vinyl butyrate, allyl alcohol, dimethylaminoethyl acrylate, dimethylaminoethyl methacrylate, phosphoethyl methacrylate, N-vinylpyrollidone, N-vinylfonnamide, N-vinylimidazole, vinyl acetate, maleic anhydride, maleic acid, maleimides, styrenics and combinations thereof. The specific compounds herein mentioned are merely illustrative and are not to be considered all-inclusive; those skilled in the art are fully familiar with the known polymerizable ethylenically unsaturated comonomers:

Preferably the percent solids of total monomers in the reaction solvent solution should be from about 5 to about 65 weight percent relative to the total weight of the monomer/solvent solution, and more preferably from about 10 to 25 weight percent. The total additional monoethylenically unsaturated monomer utilized may be from 0 to about 99 weight percent based on total weight of the monomers. In one preferred application, comonomers include about 10 percent to about 99 percent, by weight, of methyl methacrylate; and optionally, up to 20 percent, by weight, of a comonomer selected from the group consisting of methyl acrylate, ethyl acrylate, butyl acrylate, butyl methacrylate, hydroxyethyl methacrylate, acrylic acid, styrene, acrylamide, (meth)acrylonitrile, vinyl acetate, vinyl pyridine, vinylpyrrolidone, or methacrylic acid.

After the polymerization, the level of residual monomers may be reduced by adding one or more initiators or reducing agents. Preferably, any post-polymerization additions of initiators or reducing agents are conducted at or below the polymerization temperature. Generally, any of the initiators suitable for the polymerization step are also suitable for reducing the residual monomer content of the polymer mixture. The additional amount of initiator, either the same or different, may be added either in a semicontinuous fashion, or in one portion at the end of the reaction period. The molecular weight of the polymer product produced by the process of the present invention is from about 500 to about 5,000,000 molecular weight, preferably from about 50,000 to about 1,000,000 as measured by size exclusion chromatography (SEC) based on a relative polystyrene standard. A skilled practitioner will recognize that more or less initiator may be used to obtain polymers of various molecular weights. The desirable molecular weight range is for printing plate applications. Other applications may have other desirable ranges.

The polymerization product may be recovered and used as is, separated by conventional techniques to isolate the polymer solids, or diluted with water, alcohol, or other solvents to adjust the percent reaction solids to a target weight percent. If desired, excess initiator in the polymer product may be reduced with one or more common reducing agents such as sodium metabisulfite or isoascorbic acid. Additionally, the pH of the polymer product may be adjusted such as, for example, by adding a common base such as sodium hydroxide.

The polymer product produced by the process of the present invention is particularly useful as the imaging layer of a processless printing plate that is exposed and used on a press without further development. The products of the present invention may be used as made, or may be combined with other additives to enhance their performance. Such additives may include dyes, surfactants, cross-linking moieties, and the like.

The process of the invention is described in the following examples. It is understood that these examples are meant as illustrations and are not limiting in their scope.

EXAMPLES

Example 1

A one-liter three-neck flask was equipped with a mechanical stirrer, a nitrogen bleed and a condenser. The vessel was placed in a heating apparatus and the stirrer set to 100 rpm. With stirring, 88 mL of demineralized water was added to the vessel, followed by 15.90 g (0.1 mole) of sodium thiosulfate. The sodium thiosulfate was stirred until completely dissolved at room temperature. To this clear solution was added 15.26 (0.1 mole) chloromethylstyrene (a mixture of 3-and 4-chloromethylstyrene), followed by 88 grams of methanol. The mixture was heated to a gentle reflux temperature of around 70° C., under a slight positive nitrogen pressure, and stirred at this temperature for three hours. The solution was allowed to cool slowly to room temperature, and the product vinylbenzylthiosulfate monomer (25.2 g, 0.1 mole, theory) was used without further isolation or purification. NMR of a dried sample was consistent with the proposed structure, with no visible chloromethyl groups remaining.

Example 2

The process described in Example 1 was repeated using ethanol instead of methanol. The thiosulfate monomer thus obtained is used without further isolation or purification.

Example 3

The process described in Example 1 was repeated using acetone instead of methanol. The thiosulfate monomer thus obtained is used without further isolation or purification.

Example 4

The thiosulfate monomer made in Example 1 was polymerized as follows: Under stirring and positive nitrogen pressure, the solution was heated to 60° C., and 0.25 grams (1% of monomer) 2,2'-azobis(2,4-dimethylpentanenitrile) was added. The solution was heated to a gentle reflux at around 70° C., under positive nitrogen pressure, and stirred for 24 hours. The polymer product was isolated by precipitation into 1 L of isopropyl alcohol, rinsed with 100 mL isopropyl alcohol, then dried at 40° C. in a vacuum oven. The isolated yield was 20.9 g, or 83% theory. The NMR in deuterated DMSO was consistent with poly (benzylthiosulfate) with no visible residual chloromethyl groups. The molecular weight by SEC was Mn=39,200, Mw=61,400, with a polydispersity of 1.64. The white polymer product was soluble in water and acetone.

Example 5

A five-liter three-neck flask was equipped with a mechanical stirrer, an argon bleed and a condenser. The vessel was placed in a heating apparatus and the stirrer set to 100 rpm. With stirring, 120 mL of demineralized water was added to the vessel, followed by 118.6 g (0.75 mole) of sodium thiosulfate. The sodium thiosulfate was stirred until completely dissolved at room temperature. To this clear solution was added 111.4 (0.73 mole) chloromethylstyrene (a mixture of 3- and 4-chloromethylstyrene), followed by 480 grams of methanol. The mixture was heated to a gentle reflux temperature of around 70° C., under a slight argon flow, and stirred at this temperature for three hours. The solution was allowed to cool slowly to room temperature and 2120 grams of methanol was added, followed by 450 grams (4.5 moles) of methyl methacrylate. The solution was heated to 55° C. and 9.0 grams of 2,2'-azobis(2-methylpropanenitrile) were added and the clear solution stirred for 20 hours. A portion of 1.0 grams of 2,2'-azobis (2,4-dimethylpentanenitrile) was added and the solution was stirred for an additional two hours. Added 2 g of diatomaceous earth (celite) and stirred until the material cooled to RT. The product polymer solution was filtered through a glass fiber filter. The filtered polymer solution was precipitated into 15 L isopropanol, yielding 515 grams (85% theory) of a fine white powder, with a molecular weight average of 126,000 by SEC.

Example 6

A two-liter three-neck flask was equipped with a mechanical stirrer, a nitrogen bleed and a condenser. The vessel was placed in a heating apparatus and the stirrer set to 100 rpm. With stirring, 100 mL of demineralized water was added to the vessel, followed by 31.62 g (0.2 mole) of sodium thiosulfate. The sodium thiosulfate was stirred until completely dissolved at room temperature. To this clear solution was added 30.52 (0.2 mole) chloromethylstyrene (a mixture of 3- and 4-chloromethylstyrene), followed by 100 grams of 3A ethanol. The mixture was heated to a gentle reflux, under a slight positive nitrogen pressure, and stirred at this temperature for three hours. The solution was allowed to cool to 65° C. and the product vinylbenzylthiosulfate monomer (50.4 g, 0.2 mole, theory) was used without further isolation or purification. Added to this reaction mixture was 243 mL demineralized water, 243 g of 3A ethanol, 80.3 g of methyl methacrylate, and 0.39 g of AIBN initiator. The solution was heated to 75° C. and held there for 24 hours with stirring. A sample of the polymer product solution was filtered and precipitated into isopropanol and dried. NMR revealed incorporation of both monomers. Molecular weight average by SEC=284,000.

Example 7.

A two-liter three-neck flask was equipped with a mechanical stirrer, a nitrogen bleed and a condenser. The vessel was placed in a heating apparatus and the stirrer set to 100 rpm. With stirring, 200 mL of demineralized water was added to the vessel, followed by 37.42 g (0.253 mole) of ammonium thiosulfate. The ammonium thiosulfate was stirred until completely dissolved at room temperature. To this clear solution was added 38.16 g (0.250 mole) chloromethylstyrene (a mixture of 3- and 4-chloromethylstyrene), followed by 200 grams of methanol. The mixture was heated to a gentle reflux temperature of around 70° C., under a slight positive nitrogen pressure, and stirred at this temperature for three hours. The solution was allowed to cool slowly to room temperature and the product vinylbenzylthiosulfate ammonium salt monomer (61.8 g, 0.25 mole, theory) was used without further isolation or purification.

Example 8

The thiosulfate monomer made in Example 7 was copolymerized with methyl methacrylate as follows: Under stirring and positive nitrogen pressure, the solution was heated to 60° C., and 13 mL demineralized water, 439 g methanol, 112.64 g (1.125 moles) methyl methacrylate, and 0.26 grams (0.15% of monomers) 2,2'-azobis(2-methylpropanenitrile) (Vazo 64) was added. The solution was heated to a gentle reflux at around 70° C., under positive nitrogen pressure, and stirred for 24 hours. A second initiator addition was made of 0.5 g of 2,2'-azobis(2,4-dimethylpentanenitrile) (Vazo 52) and the material was heated an additional 4 hours. The polymer product was then cooled to room temperature, filtered through course cloth, and ultrafiltered to remove residual small molecules. The final aqueous product was white, 1100 grams at 13% solids, or 82% theory, based on solids. Molecular weight average by SEC=932,000.

The invention has been described with reference to a preferred embodiment; however, it will be appreciated that a person of ordinary skill in the art can effect variations and modifications without departing from the scope of the invention.

What is claimed is:

1. A method of preparing a thiosulfate salt containing polymer comprising reacting at least one thiosulfate salt with at least one halogenated styrenic monomer to form a styrenic thiosulfate salt monomer represented by Formula (1)

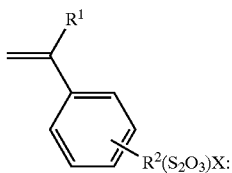

Formula (1)

wherein X is a cationic counter ion; $R^1$ is a substituent; and $R^2$ is a divalent linking group; wherein the styrenic thiosulfate monomer is not isolated or purified prior to the next step;

combining the thiosulfate monomer with at least one additional ethylenically unsaturated monomer, wherein the total additional monomer utilized is from 0 to about 99 weight percent based on the total weight of monomers;

diluting the monomers in an appropriate solvent;

adding a free radical initiator; and maintaining the reaction mixture under an air or any inert atmosphere at a reaction temperature of from about 10° C. to about 100° C. during the polymerization.

2. The method of claim 1 wherein X is sodium, potassium, magnesium, or ammonium; $R^1$ is either a hydrogen or halide atom, a substituted or unsubstituted alkyl group of 1 to 16 carbon atoms, a substituted or unsubstituted aryl group of 6 to 16 carbons, a substituted or unsubstituted heteroaryl group of 4 to 16 atoms, or a cyano group; and $R^2$ is a substituted or unsubstituted alkylene group of 1 to 8 carbon atoms that can have one or more oxygen, nitrogen or sulfur atoms in the chain, or a substituted or unsubstituted arylenealkylene group of 7 to 16 carbons.

3. The method of claim 1 wherein the free radical initiator is a peroxide or an azo.

4. The method of claim 1 wherein an additional amount of initiator, either the same or different, is added either in a semicontinuous fashion or in one portion at the end of the reaction period.

* * * * *